United States Patent [19]
Kaufhold, Jr. et al.

[11] Patent Number: 5,125,898
[45] Date of Patent: Jun. 30, 1992

[54] DISPOSABLE SYRINGE WITH AUTOMATIC NEEDLE RETRACTION

[75] Inventors: Harry Kaufhold, Jr., 9711 Ebb St., Houston, Tex. 77089; Martin Jasso, Houston; Gerald E. Kruckeberg, Cypress, both of Tex.

[73] Assignee: Harry Kaufhold, Jr., Houston, Tex.

[21] Appl. No.: 776,843

[22] Filed: Oct. 15, 1991

Related U.S. Application Data

[63] Continuation-in-part of Ser. No. 497,458, filed as PCT/US91/01768, Mar. 15, 1991, Pat. No. 5,000,736.

[51] Int. Cl.⁵ .............................................. A61M 5/32
[52] U.S. Cl. ..................................... 604/110; 604/195
[58] Field of Search .............. 604/110, 192, 195, 198, 604/263, 187, 241–243

[56] References Cited

U.S. PATENT DOCUMENTS

| | | | |
|---|---|---|---|
| 3,008,570 | 11/1961 | Roehr et al. | 206/43 |
| 3,107,785 | 10/1963 | Roehr et al. | 206/63.2 |
| 3,895,633 | 7/1975 | Bartner et al. | |
| 3,976,069 | 8/1976 | Ong . | |
| 4,300,678 | 11/1981 | Gyure et al. | 206/364 |
| 4,356,822 | 11/1982 | Winstead-Hall | 128/215 |
| 4,425,120 | 1/1984 | Sampson et al. | 604/198 |
| 4,592,744 | 6/1986 | Jagger et al. | 604/192 |
| 4,639,249 | 1/1987 | Larson | 604/198 |
| 4,643,200 | 2/1987 | Jennings | 128/763 |
| 4,655,751 | 4/1987 | Harbaugh | 604/198 |
| 4,666,435 | 5/1987 | Braginetz | 604/198 |
| 4,675,005 | 6/1987 | DeLuccia | 604/110 |
| 4,692,156 | 9/1987 | Haller | 604/195 |
| 4,723,943 | 2/1988 | Spencer | 604/198 |
| 4,738,663 | 4/1988 | Bogan | 604/198 |
| 4,747,830 | 5/1988 | Gloyer et al. | 604/110 |
| 4,790,822 | 12/1988 | Haining | 604/110 |
| 4,816,022 | 3/1989 | Poncy | 604/198 |
| 4,826,483 | 5/1989 | Molnar, IV | 604/110 |
| 4,840,619 | 6/1989 | Hughes | 604/187 |
| 4,950,241 | 8/1990 | Ranford | 604/110 |
| 4,950,251 | 8/1990 | Haining | 604/195 X |
| 5,000,736 | 3/1991 | Kaufhold, Jr. et al. | 604/110 |

*Primary Examiner*—John D. Yasko
*Attorney, Agent, or Firm*—William E. Shull

[57] ABSTRACT

A disposable medicinal syringe including a tubular plunger from which air has been evacuated and a seal member releasably attached on the distal end of the plunger. The plunger is slidingly and sealingly disposed in the barrel of the syringe. A luer lock assembly is mounted within the barrel and includes a releasable hub portion which is securely engageable with the releasable plunger seal member, the securely engaged members when released being actuated by ambient air pressure into retraction into the evacuated plunger. The luer lock assembly is adapted for receiving a hypodermic needle or other medical device. Following use of the syringe, longitudinal axial force is applied to the proximal end of the plunger, thereby detaching, in sequence, first and second annular thin-walled portions of the luer lock assembly to release the hub portion for movement within the barrel, securely mounting the plunger seal member into the luer lock hub, and detaching the plunger seal member from the plunger at an annular thin-walled portion. The combined luer lock hub/plunger seal member and attached needle or other medical device are then forced into the evacuated interior of the plunger, safely isolating the needle or other medical device inside the plunger.

12 Claims, 3 Drawing Sheets

DISPOSABLE SYRINGE WITH AUTOMATIC NEEDLE RETRACTION

This is a continuation-in-part of copending application Ser. No. 07/497,458 filed as PCT/US91/01768, Mar. 15, 1991 now U.S. Pat. No. 5,000,736.

BACKGROUND OF THE INVENTION

The present invention relates to the invention described and claimed in U.S. Pat. No. 5,000,736, issued Mar. 19, 1991, to Kaufhold et al., the disclosure of which is hereby incorporated by reference, and to the invention described and claimed in pending International application Ser. No. PCT/US91/01768, filed Mar. 15, 1991, of Kaufhold et al., the disclosure of which is hereby incorporated by reference, as well. The present application is owned by Applicant Kaufhold, the assignee of the above-referenced patent and application. The present application comprises a continuation-in-part of the above-referenced application and/or patent, and the priority and other benefits of the filing dates of such application and patent are hereby claimed.

The present invention relates generally to medical instruments, and more particularly to a safety-disposable medicinal syringe. Still more particularly, the present invention relates to a disposable syringe having a releasable luer lock member securely engageable with a releasable plunger distal seal member, the securely engaged members when released being actuated by ambient air pressure into retraction into an evacuated plunger. The luer lock member/plunger distal seal member assembly carries with it into the evacuated plunger a medical device, such as a hypodermic needle, which is mounted to the luer lock member in order to safely isolate the needle or other medical device inside the plunger.

A problem for doctors, nurses, and other health care personnel who use or handle medicinal syringes is accidental puncture of the skin by the needle. The problem can be very serious if the needle has been used. Potentially fatal diseases, such as hepatitis or Acquired Immune Deficiency Syndrome (AIDS), can be contracted if the needle has been used on an infected subject.

The syringe needle is typically covered with a removable sheath prior to and following use to prevent accidental contact, but the act of replacing the sheath after use can still result in accidental skin puncture. Also, if the sheath is not securely repositioned, the danger exists that personnel subsequently involved in disposal of the device may become infected by accidental puncture.

Solutions that attempt to better protect the health care worker include that disclosed in U.S. Pat. No. 4,790,822. The '822 patent discloses a disposable syringe in which the needle can be first captured by the plunger and then withdrawn into the barrel in a position with the needle completely protected by the barrel. The plunger can then be broken off, leaving the broken end flush with the end of the barrel, so that the needle cannot be accidentally pushed out from the barrel and exposed.

U.S. Pat. No. 4,747,830 discloses a similar system, with a plunger that can be broken off once the needle is retracted into the barrel. U.S. Pat. Nos. 4,692,156 and 4,675,005 both disclose disposable syringes wherein the needle can be retracted into the barrel. U.S. Pat. No. 4,643,200 discloses a similar system, used with a blood donor assembly, which allows retraction of a needle into a barrel.

U.S. Pat. No. 4,425,120 discloses a needle guard movable on the syringe barrel between an extended position in which the needle guard shields the needle and a retracted position in which the needle is exposed for use. U.S. Pat. No. 4,816,022 discloses a syringe with a sliding cap for preventing accidental puncture. The '022 patent utilizes a nub and backseat for engagement of a nosepiece for securing the cap around the syringe for safety purposes. U.S. Pat. No. 3,008,570 discloses use of a removable cap for the purpose of enclosing and protecting a sterilized syringe in a transport. U.S. Pat. No. 4,840,619 discloses a syringe assembly that has a transport held in telescoping position over a syringe by flanges. Other and various means of sheathing or shielding a syringe are shown in the following U.S. Pat. Nos.: 4,738,663; 4,723,943; 4,666,435; 4,655,751; 4,639,249; 4,592,744; 4,356,822; 4,300,678; 3,976,069; 3,895,633; 3,107,785. U.S. Pat. No. 4,826,483 discloses a non-reusable syringe with a one-way movable piston.

The present invention improves upon these devices by providing a means of automatically, without the need of unusual manipulation, rendering a used syringe safe for handling immediately after use and throughout subsequent disposal procedures, as well as rendering it unsuitable for further use.

SUMMARY OF THE INVENTION

The present invention comprises a medicinal syringe including a tubular plunger from which air has been evacuated and a seal member releasably attached on the distal end of the plunger. The plunger is sealingly slidably disposed in a tubular barrel. A luer lock assembly is releasably attached within the distal end of the barrel. A medical device such as a hypodermic needle is mounted in the distal portion of the luer lock assembly, according to conventional techniques. Upon application of a predetermined longitudinal axial force to a first proximal face of the luer lock assembly, a first annular thin walled portion of the luer lock assembly ruptures, releasing the luer lock assembly from the inside wall of the barrel. Continued application of a longitudinal axial force to said first proximal face of the luer lock assembly pushes the luer lock assembly distally until a distal face of the luer lock assembly engages a shoulder in the distal end portion of the barrel. Upon continued application of a predetermined longitudinal axial force to said first proximal face of the luer lock assembly, a second annular thin walled portion of the luer lock assembly ruptures, the second annular thin walled portion being concentric with and smaller in diameter than the first annular thin walled portion, and smaller in diameter than the inside diameter of the plunger. Rupture of the second annular thin walled portion releases a ring shoulder, comprising part of the luer lock assembly the inside diameter of which corresponds to the second annular thin walled portion and the outside diameter of which corresponds to the first annular thin walled portion, for movement into an annular recess in the distal end portion of the barrel, away from contact with the plunger. The central hub portion of the luer lock assembly is thereby released for movement within the barrel. Continued application of longitudinal axial force on the plunger causes the secure engagement of the plunger distal seal member with the released central hub portion of the luer lock assembly, which is restrained from distal movement by the shoulder in the distal end portion of the barrel. Continued application of a predetermined longitudinal axial force on the plunger ruptures an annular thin walled portion of the plunger distal seal member, the diameter of the thin walled portion being smaller than the inside diameter of the plunger tube. This releases the central hub portion of the plunger distal seal member for movement within the plunger. The released central hub portion of the plunger distal seal member, which is securely engaged with the released central hub portion of the luer lock assembly, will be forced by the differential pressure between the vacuum inside the plunger and the ambient air into the interior of the tubular plunger, carrying the needle with it. Once forced into the tubular plunger, the needle and the members to which it is attached will remain there indefinitely, thus eliminating accidental puncturing by the needle of a person in the vicinity of the syringe.

In its preferred embodiment, the invention is used in accordance with standard procedures for the subcutaneous, intramuscular, of intravascular injection or aspiration of substances into or out of the body, which procedures are well known to those schooled in the art. Immediately following the procedure, longitudinal axial force is applied to the proximal end of the plunger, thereby detaching, in sequence, the first and second annular thin walled portions of the luer lock assembly, securely mounting the plunger distal seal member into the luer lock assembly, detaching the annular thin walled portion of the plunger distal seal member, and forcing the combined luer lock/plunger distal seal assembly and its attached needle into the evacuated interior of the plunger. The needle is then retained in the evacuated center of the plunger indefinitely, rendering it incapable of puncturing the skin of the primary user or of personnel involved in secondary handling of the device.

The invention will now be described in further detail with reference to the accompanying drawings.

DETAILED DESCRIPTION OF THE PREFERRED EMBODIMENT OF THE INVENTION

Figure 1:
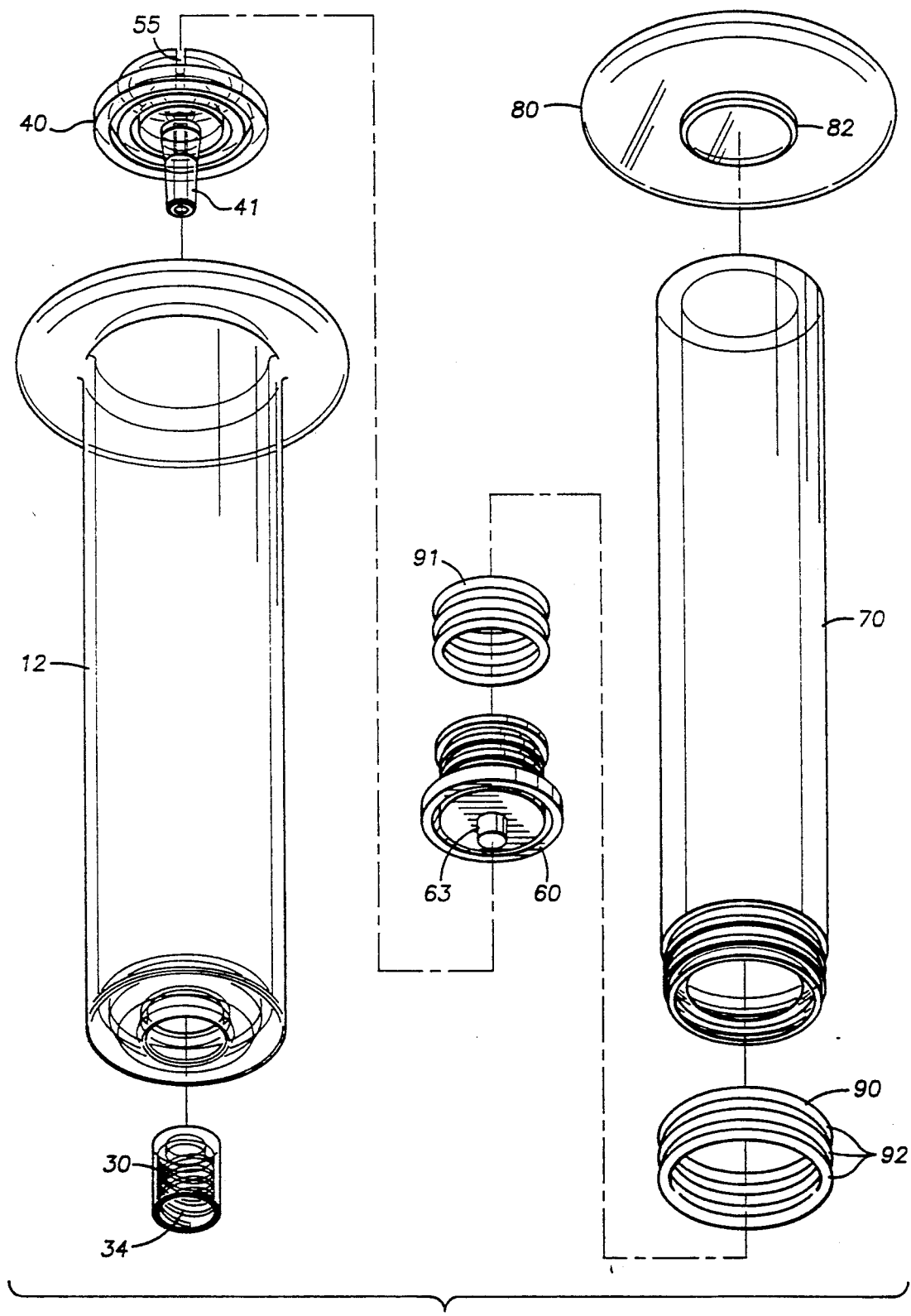
FIG. 1 is an exploded pictorial view of a syringe of a preferred embodiment of the invention.

While the invention is satisfied in many different forms, there is shown in the drawings and will herein be described in detail preferred embodiments of the invention, with the understanding that the present disclosure is to be considered as exemplary of the principles of the invention and is not intended to limit the scope of the invention to the embodiments illustrated.

Figure 2:
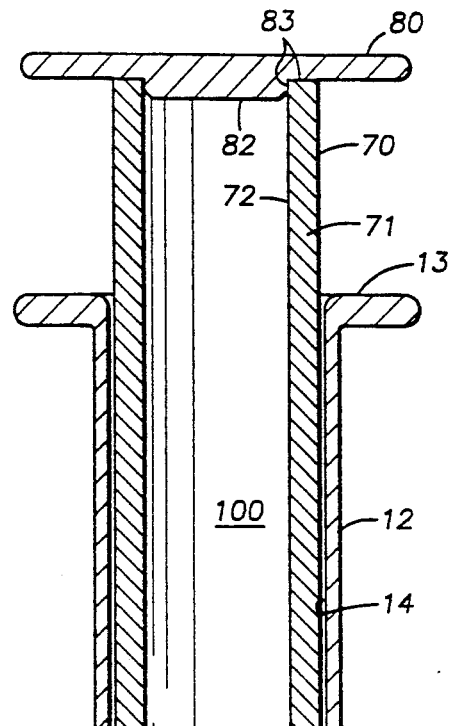
FIG. 2 is a longitudinal vertical cross-sectional view of the syringe of FIG. 1 prior to actuation of the automatic needle retraction means.

Referring now to FIGS. 1 and 2, there is shown a disposable syringe with automatic needle retraction of the present invention, comprised of barrel 12, luer thread bushing 30, luer taper seal projection member 40, plunger tube 70, plunger distal seal 60, thumb button seal 80, vacuum seal gasket 91, and grommet 90.

Barrel 12 comprises a cylindrical tube of plastic or the like with flange 13 at its proximal end. The inner wall 14 of barrel 12 is straight and uniform through most of the length of barrel 12, and includes an inner shoulder 15 near the distal end of barrel 12. The distal end of barrel 12 includes inner surfaces 17, 18, 19, 20, and 21 to form a compound wall recess 16 which is circumferentially disposed within the distal end of the barrel. Wall portion 21 terminates in an annular shoulder 22, and cylindrical walls 24 extend from shoulder 22 to the distal terminal end of barrel 12 to form cylindrical opening 23. The diameter of opening 23 is sufficient to permit luer thread bushing 30 to fit loosely therethrough without contacting barrel wall 24.

Referring additionally to FIGS. 3-7, luer taper seal projection member 40 preferably comprises a plastic molded piece with compound hollow tapered projection 41. Surface 42 defines a conventional luer slip taper common to other slip luer devices as used in medical accessories and devices. Outer surface 43 of the taper projection 41 is cylindrical and of such diameter that it will fit tightly against walls 32 of bore 31 of bushing 30 resulting in a slip fit contact between wall 43 of the taper projection and wall 32 of the luer thread bushing 30. The slip fit assures that luer thread bushing 30 will align concentrically over the luer taper seal projection 41.

Luer taper seal projection member 40 includes a circular disc member 47 around its proximal end. The disc 47 has annular grooves 48 and 49 on one or both of its distal and proximal faces, for example on its distal face as shown in the drawings. The grooves, shown as angular cuts, are of such depth that at their apexes they form thin walled sections 56 on the disc 47. Although angular cuts are shown for grooves 48, 49, it should be understood that other shapes could be used for the groove profiles. The outer diameter of groove 49 is smaller than the inside diameter of the plunger tube so that the central hub portion of member 40 when released will slide into the evacuated interior of the plunger tube.

The proximal face of the luer taper seal projection member 40 includes a circumferentially disposed outer slotted ring projection 50, concentrically disposed with respect to disc 47. More centrally and similarly disposed on the proximal face of the member 40 is an inner slotted ring projection 52. Slot 55 is preferably one of eight such slots that are circumferentially spaced apart and extend longitudinally axially in the rings 50, 52 from their proximal end faces. Slots 55 are cut through both ring projections 50, 52 to a depth that is preferably at least tangent with proximal face 57 of disc 47. Recess 58 is a tapered pocket formed by wall 54. This tapered pocket is shaped correlatively to a tapered projection 63 disposed on plunger distal seal 60 such that when these features 58, 63 are mated, the plunger distal seal 60 will become locked to the luer taper seal projection member 40.

Luer thread bushing 30 is a conventionally configured molded plastic piece having a through hole 31 defined by wall 32 on its proximal end. The through hole 31 diameter is such that it mates with surface 43 of the luer taper seal projection member 40. Wall 32 forms a tight slip fit on surface 43 of the luer taper seal. Internal threads 34 are adapted to mate with conventional luer locking medical devices. When luer projection member 40 and luer thread bushing 30 are mated and bonded in the region of luer thread bushing face 33 and walls 32, a conventional luer lock assembly is formed by the thread 34 and taper projection 41.

Plunger tube 70 includes an internal cylindrical surface 72 and distal counterbore 73. The counterbore 73 will accept flange 61 of plunger distal seal 60. The outer surface 74 of plunger tube 70 at its distal end will accept a soft rubber grommet 90. Grommet 90 may comprise a unitary member having a plurality of annular ridges 92 similar to "O" rings, but any seal configuration may be used, including "O" rings disposed in appropriate grooves, so long as a fluid tight seal is obtained between barrel 12 and plunger tube 70. The plunger tube 70 is made of plastic or other material suitable to hold a vacuum for extended periods, for example, greater than one year. The wall 71 of the plunger tube may be multilayer molded or multiextruded to form a barrier wall resistive to air permeability.

Plunger distal seal 60 includes a tapered projection 63 on its distal end, designed to lock into the tapered cavity 58 of the luer taper seal projection member 40. The length of the projecting member 63 is preferably less than the depth of the taper cavity 58 to assure a positive locking of the plunger seal 60 and luer member 40 when the two members are compressed together. An annular, angularly cut groove 62 or grooves is/are circumferentially disposed in one or both of the proximal or distal faces of the flange 61 of the plunger distal seal 60, for example in the distal face as shown in the drawings. The groove 62 has such depth as to produce a predetermined reduction in wall thickness of the flange at the apex of the groove. The outer diameter of groove 62 is smaller than the inside diameter of the plunger tube so that the central hub portion of member 60 when released will slide into the evacuated interior of the plunger tube. The groove 62 thus forms a breakable ring groove calibrated to break at the application of longitudinal axial force preferably greater than that required to rupture the reduced wall thickness portions at grooves 48 and 49 of the luer member 40. As in the case of grooves 48 and 49, the groove(s) 62 may have any suitable profile other than the particular angular cut profile shown in the drawings.

The outer surface 64 of plunger distal seal 60 is configured to accept a vacuum seal gasket 91 similar in form and function to grommet 90. Gasket 91 forms a seal between member 60 and the inside diameter wall 72 of plunger tube 70. Recess 68 in the proximal end of member 60 serves to reduce its mass and thus facilitate its movement within plunger tube 70 upon actuation. Although the distal face of member 60 adjacent projection 63 is shown in the drawings as substantially flat, that distal face could have any of a number of other shapes, such as conical or tapered. Similarly, the disc 47 of member 40, and the distal end portion of barrel 12, may be tapered or frustoconical as well, in order to facilitate the draining of fluids from the interior of the syringe of the present invention.

Thumb button seal 80 preferably comprises a plastic molded disc. Distally and concentrically disposed on the thumb button seal 80 is a cylindrical projection 82. The diameter of projection 82 is such that it forms an interference fit within the internal diameter walls of the proximal end of plunger tube 70. This interference fit is used to advantage in the friction bonding of the thumb button seal 80 to the plunger tube 70, which process is performed in a vacuum atmosphere.

Thus, it is seen that an evacuated plunger assembly is formed by joining the plunger tube 70, plunger distal seal 60 with its gasket 91, thumb button seal 80, and grommet 90. Gasket 91 forms an air tight seal against plunger tube internal surface 72, and this seal becomes a sliding seal when the device of the present invention is actuated, as described below. The plunger distal seal 60 is bonded to the plunger tube 70 at region 93 by an adhesive, ultrasonic welding, or other suitable means. Thus an air tight seal is formed by the bond, and is augmented by the gasket 91.

To form a vacuum 100 in the plunger assembly, the distally sealed plunger is placed in a vacuum atmosphere. While in the vacuum, the thumb button seal 80 is bonded to the proximal end of the plunger tube 70. The bond is formed in region 83 by friction spin welding, ultrasonic welding or other suitable means. Thus a vacuum 100 is formed inside the cylindrical plunger assembly. Grommet 90, circumferentially disposed on the distal outer surface of plunger tube 70, forms a slidable seal on the internal surface 14 of barrel 12.

The assembly comprising luer taper seal 40 and luer thread bushing 30 is bonded to the internal distal end of barrel 12. The luer thread bushing 30 is bonded to the luer taper seal 40 in region 37 by friction spin welding, ultrasonic welding, adhesive bonding or other suitable means. The resulting luer assembly is then introduced into the barrel 12 through its proximal end opening and advanced to the position shown in FIG. 2. When the luer assembly contacts internal shoulder 15 of barrel 12, the luer assembly is bonded to the barrel by means such as those previously stated for other assemblies. The seal bond between members 12, 40 is formed in region 94.

It can be seen that any medical device having a standard luer slip or luer lock, such as a hypodermic needle (shown in phantom lines in the drawings), will mate to the distal end of the syringe of the present invention. Longitudinal axial movement of the plunger assembly within the barrel, such movement being sealed via slidable seal grommet 90, causes the filling or emptying of cavity 102 of the syringe of the present invention via bore 46 of the luer taper seal projection member 40.

Figure 3:
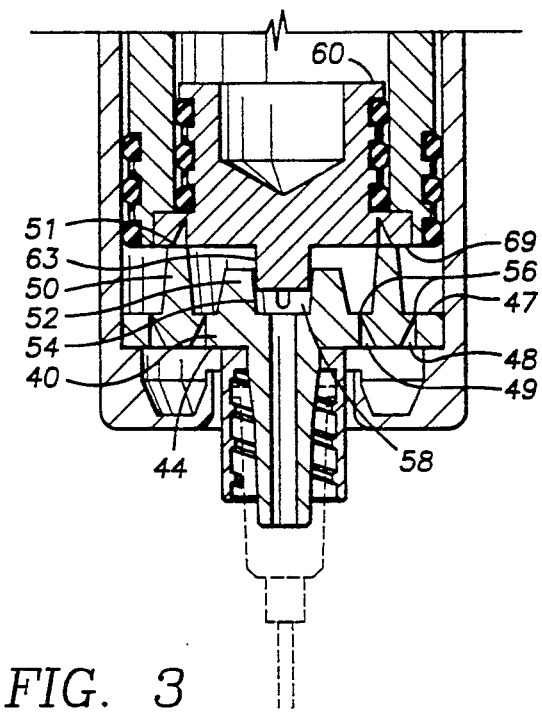
FIG. 3 is a longitudinal, vertical, enlarged cross-sectional view of the distal end portion of the syringe of FIGS. 1 and 2 following use of the syringe and upon commencement of actuation of the automatic needle retraction means of the invention.

Referring particularly to FIGS. 3–7, a used needle (again, shown in phantom lines) attached to the luer lock assembly may be drawn into vacuum 100 by sequentially rupturing grooves 48, 49, locking projecting taper 63 into taper recess 58, rupturing groove 62, and allowing atmospheric pressure to force the needle into the evacuated plunger tube. Following use of the syringe, forcing the plunger 70 fully into the barrel 12 causes the distal face 69 of plunger distal seal 60 to apply pressure on surface 51 of the luer taper seal projection member 40. All of the force is applied to the thin wall 56 at the apex of groove 48, grooves 49 and 62 not yet being affected. This configuration is shown in FIG. 3. When sufficient force is applied, this causes the thin wall at groove 48 to rupture.

Figure 4:
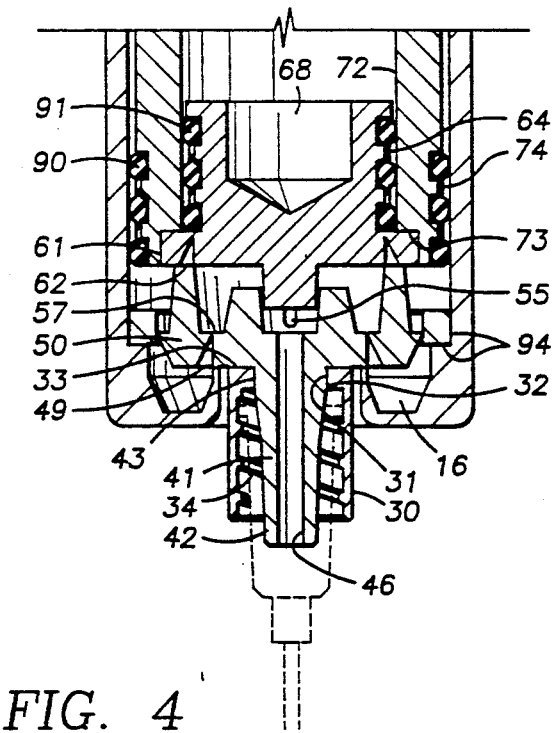
FIG. 4 is a view similar to FIG. 3, showing the first annular thin walled portion of the luer taper seal projection member having been ruptured, and the luer lock assembly moved distally into engagement with the shoulder in the distal end of the barrel.

Release of luer taper segment 40 at groove 48 allows the assembly to be pushed farther, distally, into the barrel until surface 44 of member 40 strikes annular shoulder surface 22 of the barrel 12. This configuration is shown in FIG. 4. At this instant, upon continued axial force being applied in a distal direction on plunger 70, ring groove 49 now bears the total applied force and the thin wall at its apex is caused to rupture, releasing ring shoulder 50.

The continued movement of the plunger into the barrel forces the released ring shoulder 50 to drop into distal barrel ring recess 16. Recess 16 is of such depth that the ring shoulder 50 is removed from contact with the plunger tube 70 and the plunger distal seal 60.

Figure 5:
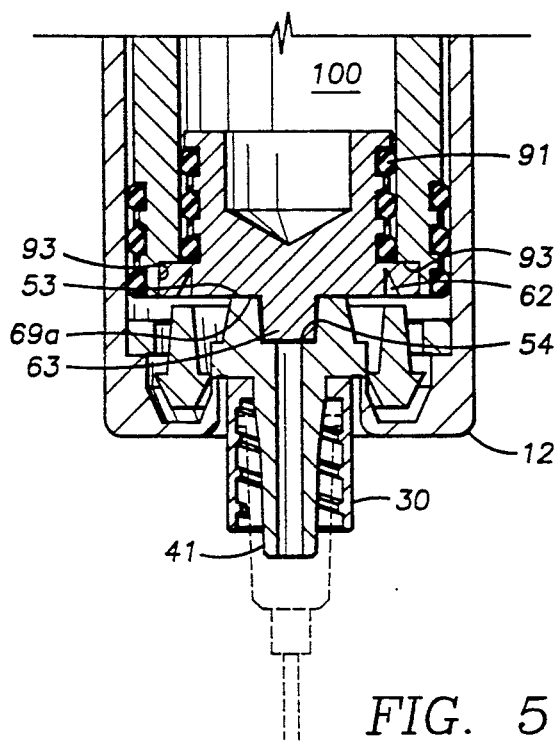
FIG. 5 is a view similar to FIGS. 3 and 4, showing the second annular thin walled portion of the luer taper seal projection member having been ruptured, and the plunger distal seal member securely engaged with the luer taper seal projection member.

Continued distal movement of the plunger into the barrel forces tapered projection 63 to lock into tapered recess 58. At this time the longitudinal, distal axial force is applied to the contacting surfaces of the tapered projection 63 and tapered recess 54. Additionally, surface 69a contacts surface 53 when the tapered features 63, 54 are fully mated. This configuration is shown in FIG. 5.

Figure 6:
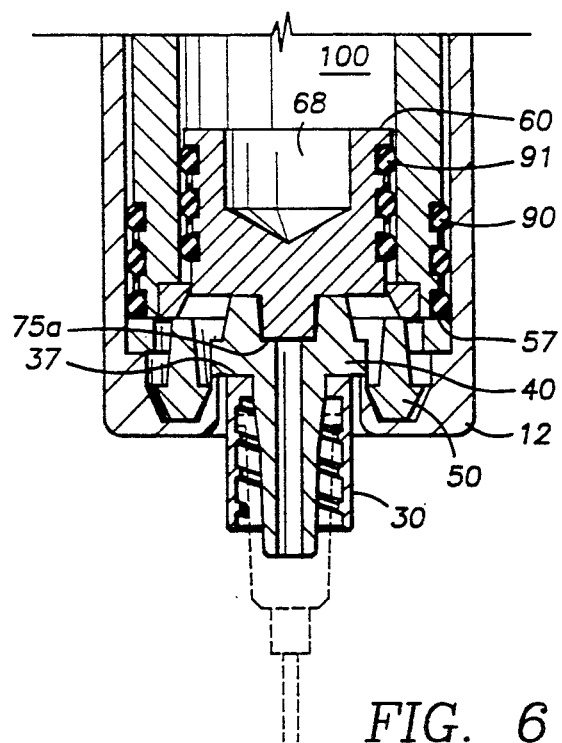
FIG. 6 is a view similar to FIGS. 3, 4, and 5, with the annular thin walled portion of the plunger distal seal member having been ruptured.
Figure 7:
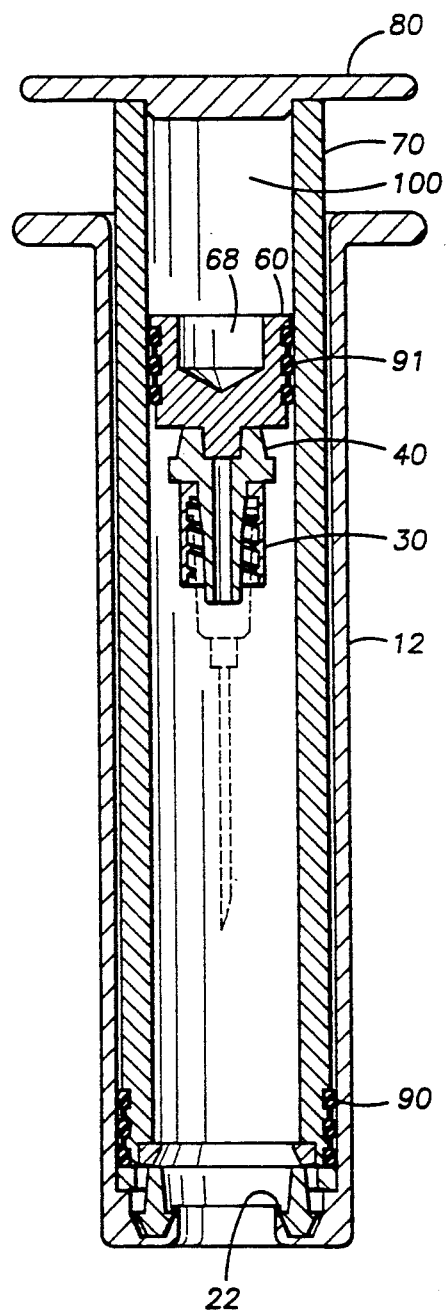
FIG. 7 is a longitudinal vertical cross-sectional view of the syringe of FIGS. 1-6 upon completion of the actuation of the automatic needle retraction means of the invention.

The central-most segment or central hub portion of member 40 is supported against barrel surface 22 and unable to move farther distally. The longitudinal, externally applied force effecting the continued distal, axial movement of the plunger into the barrel is now transferred to the plunger distal seal 60. The applied force is borne by the thin wall at the apex of groove 62 on the plunger distal seal 60 until a predetermined load limit is exceeded, causing the thin wall to rupture. This is shown in FIG. 6. At the instant when the thin wall at the apex of groove 62 ruptures, the central segment or central hub portion of the distal seal 60 is forced into vacuum space 100 by the continued movement of the plunger into the barrel and the effect of atmospheric pressure. The result is shown in FIG. 7.

Mechanical force is applied, along with force due to pressure differentials, to move the central hub portion of the distal seal 60 into the plunger tube at the instant when groove 62 ruptures. The distal surface of the released hub portion of plunger seal 60 is locked to the proximal surface of the released hub segment of the luer taper seal projection member 40. As the plunger tube 70 continues to move distally into the barrel, the distal end surface of grommet 90 compresses against surface 57, which is a portion of the luer taper seal projection member 40 still attached to the barrel's distal internal surface. Since surface 22 of the barrel is holding the central or hub portion of the luer taper seal projection member 40 and preventing its further distal movement, the released central hub portion of the plunger distal seal 60 is mechanically pushed into the vacuum space 100 and gasket 91 starts to slide in a proximal direction within the plunger tube 70.

Atmospheric air pressure exists on all exposed distal surfaces of the luer thread bushing 30, the luer taper seal projection member 40, the attached needle, and the plunger distal seal 60, including its projecting taper surface 75a. When groove 62 ruptures the differential pressure between atmosphere and vacuum 100 forces the central hub pieces of the member 40 and plunger seal 60 to be driven into the vacuum space 100. The effect of the mechanical force and differential pressure is to cause the released central hub segment of distal plunger seal 60 and the released central hub segment of member 40 attached thereto, along with the attached luer thread bushing 30 and the attached needle, to be forced into the vacuum space 100 of the plunger tube 70. Gasket 91 serves to maintain a slidable seal against the inner wall surface of the plunger tube and prevent the inrush of air from compromising the vacuum 100. Thus, the vacuum-to-atmosphere differential pressure is sustained from initial rupture of seal ring groove 62 until the slidable segments are fully forced into the evacuated interior of the plunger tube.

Once the released portions of the plunger distal seal 60 and the member 40, the luer thread bushing 30, and the attached needle are disposed in the interior of plunger tube 70, they are held securely within the plunger tube to permit safe disposal of the used syringe. It is by means of the described sequence of events that the used syringe may be disposed of without unusual user action in order to effectively eliminate the risk of needle stick accidents.

Having described certain embodiments of the present invention, many modifications thereof may be made within the scope of the inventive concept taught herein and set out in the following claims. The preferred embodiments described in the foregoing specification are exemplary only, and not limiting. The scope of protection herein sought also includes all equivalents of the subject matter of the claims.

We claim:

1. A disposable syringe assembly, comprising:
   a barrel having a proximal end and a distal end and an internal central bore;
   a tubular plunger having a closed proximal end, said plunger being telescopingly insertable within the proximal end of said central bore of said barrel and adapted for sealed, sliding reciprocating movement therewithin;
   needle attachment means mounted around the inner wall of said barrel, said needle attachment means being adapted for receiving a hypodermic needle mountable therein and having a releasable hub portion adapted for movement within said central bore of said barrel when released;
   a plunger distal seal member mounted on the distal end of said tubular plunger, said plunger distal seal member having a releasable hub portion adapted for sealed sliding movement within said tubular plunger when released, said plunger distal seal member closing and sealing the distal end of said plunger prior to release of said hub portion of said plunger distal seal member, the interior of said tubular plunger being relatively evacuated;
   said releasable hub portions of said needle attachment means and said plunger distal seal member being releasable in sequence and lockingly engageable with one another upon application of a predetermined longitudinal axial force on said plunger, the distal end of said barrel having an opening therein exposing the distal faces of said releasable hub portions of said plunger distal seal member and said needle attachment means to the atmosphere;
   said releasable hub portions of said needle attachment means and said plunger distal seal member being forced, when engaged with one another and released, into the relatively evacuated interior of said plunger by differential pressure between said evacuated interior and the atmosphere.

2. The disposable syringe assembly of claim 1, wherein said predetermined force is imparted by longitudinal distal movement of said plunger within said barrel.

3. The disposable syringe assembly of claim 1, wherein said needle attachment means includes a substantially circular disc portion mounted to said inner wall of said barrel around its circumferential periphery, said disc portion having a first annular groove in one of its distal and proximal faces forming a first thin-walled disc portion, and a second annular groove in one of the distal and proximal faces of said disc forming a second thin-walled disc portion, said second annular groove being substantially concentric with and smaller in diameter than said first annular groove and smaller in diameter than the inside diameter of said tubular plunger, said releasable hub portion of said needle attachment means being circumscribed by said second thin-walled disc portion.

4. The disposable syringe assembly of claim 3, wherein said needle attachment means includes a central axial bore extending from its proximal end through its distal end, and said disc portion of said needle attachment means includes an annular, longitudinally axially extending outer projection ring disposed on its proximal face between said first and second annular thin-walled disc portions and an annular, longitudinally axially extending inner projection ring surrounding said central axial bore of said needle attachment means within and substantially concentric with said outer projection ring, the proximal end face of said outer projection ring extending proximally beyond the proximal end face of said inner projection ring.

5. The disposable syringe assembly of claim 4, wherein said outer projection ring and said inner projection ring each include side walls and at least one axially extending slot through its respective side wall, said slot in said outer projection ring communicating between the area within said barrel and outside of said outer projection ring and the annular space between said outer projection ring and said inner projection ring, and said slot in said inner projection ring communicating between said central axial bore of said needle attachment means and said annular space between said outer projection ring and said inner projection ring.

6. The disposable syringe assembly of claim 4, wherein said hub portion of said needle attachment means includes first locking means disposed on its proximal end within said inner projection ring for lockingly engaging correlatively shaped second locking means disposed on the distal end of said hub portion of said plunger distal seal member when said two hub portions are compressed together.

7. The disposable syringe assembly of claim 6, wherein said first locking means comprises a tapered pocket forming part of said bore of said needle attachment means within said inner projection ring, and wherein said second locking means includes a tapered projection disposed on the distal end of said hub portion of said plunger distal seal member, said tapered projection being insertable within said tapered pocket and being frictionally retained therein when said pocket and said projection are compressed together.

8. The disposable syringe assembly of claim 6, wherein said barrel includes an annular shoulder extending longitudinally axially in a proximal direction from the distal end of said barrel and spaced from the inner wall of said barrel, said annular shoulder being engageable with a distal face of said needle attachment means, and an annular recess disposed in the distal end of said barrel between said annular shoulder and the inner wall of said barrel, said first annular thin-walled disc portion being rupturable when said plunger engages said proximal end of said outer projection ring and upon application of a predetermined longitudinal axial force on said plunger, said needle attachment means then being movable distally upon continued application of longitudinal axial force on said plunger until a distal face of said needle attachment means engages said annular shoulder of said barrel, said second annular thin-walled disc portion then being rupturable upon application of a predetermined longitudinal axial force on said plunger against said proximal end of said outer projection ring, the portions of said needle attachment means between said first and second thin-walled disc portions including said outer projection ring then being movable into said annular recess in said barrel away from contact with said plunger, the plunger and the hub portion of the needle attachment means then being movable toward one another upon continued application of longitudinal axial force on said plunger and said first and second locking means being actuable to lock said releasable hub portions of said plunger distal seal member and said needle attachment means together.

9. The disposable syringe assembly of claim 8, wherein said plunger distal seal member includes a substantially circular disc portion mounted to the wall of said plunger around its circumferential periphery, said disc portion of said plunger distal seal member having an annular groove in one of its distal and proximal faces forming an annular thin-walled plunger seal disc portion, said annular thin-walled plunger seal disc portion having a diameter smaller than the inside diameter of said plunger and circumscribing said releasable hub portion of said plunger distal seal member, said thin-walled plunger seal disc portion being rupturable after movement of said outer projection ring into said barrel recess and locking of said two hub portions together has occurred, upon application of a predetermined longitudinal axial force on said plunger against the proximal end of said hub portion of said needle attachment means, said hub portion of said needle attachment means being restrained from further distal movement by said annular barrel shoulder.

10. The disposable syringe assembly of claim 1, wherein said needle attachment means comprises a luer lock assembly.

11. The disposable syringe assembly of claim 1, wherein said releasable hub portion of said plunger distal seal member includes a recess in its proximal end face for reducing its mass.

12. The disposable syringe assembly of claim 1, wherein said releasable hub portion of said plunger distal seal member includes a seal gasket around its circumferential periphery, said seal gasket comprising a unitary body having a plurality of longitudinally axially spaced apart seal ridges for sealingly and slidingly engaging the inner wall of said tubular plunger.

* * * * *